United States Patent
Takeuchi

(10) Patent No.: US 8,241,568 B2
(45) Date of Patent: Aug. 14, 2012

(54) REACTION TANK

(75) Inventor: Tomohiko Takeuchi, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 310 days.

(21) Appl. No.: 12/255,207

(22) Filed: Oct. 21, 2008

(65) Prior Publication Data

US 2009/0047184 A1 Feb. 19, 2009

Related U.S. Application Data

(63) Continuation of application No. PCT/JP2007/058068, filed on Apr. 12, 2007.

(30) Foreign Application Priority Data

Apr. 21, 2006 (JP) ................................. 2006-118095

(51) Int. Cl.
G05D 22/00 (2006.01)

(52) U.S. Cl. ................ 422/65; 422/64; 422/63; 422/50; 422/105; 422/106; 422/500; 422/565; 422/114; 422/129; 436/180; 436/43

(58) Field of Classification Search .................. 422/106, 422/114, 129, 63, 64, 50, 105, 500, 565, 422/65; 436/180, 43
See application file for complete search history.

(56) References Cited

U.S. PATENT DOCUMENTS

| 5,256,376 | A * | 10/1993 | Callan et al. ................... 422/102 |
| 7,842,237 | B1 * | 11/2010 | Shibuya et al. ................. 422/64 |
| 2004/0151628 | A1 * | 8/2004 | Honkanen et al. .............. 422/63 |

FOREIGN PATENT DOCUMENTS

| JP | 11-89559 A | 4/1999 |
| JP | 11-248607 | 9/1999 |
| JP | 2003-057156 | 2/2003 |
| JP | 2003-107364 A | 4/2003 |
| WO | WO 01/51929 A1 | 7/2001 |

OTHER PUBLICATIONS

Japanese Office Action for Application No. 2006-118095, dated Sep. 30, 2011, 2 pages.

* cited by examiner

*Primary Examiner* — In Suk Bullock
*Assistant Examiner* — Sharon Pregler
(74) *Attorney, Agent, or Firm* — Kilpatrick Townsend & Stockton LLP

(57) ABSTRACT

A reaction tank for causing a reaction for analyzing a specimen in a humidity-applied atmosphere in a storage vessel, includes a humidifying unit that includes a water reservoir reserving water and a humidifier releasing moisture of the water reservoir to an inside of the storage vessel, the humidifying unit humidifying the inside of the storage vessel, and a humidity detector that detects humidity inside the storage vessel. An operation of the humidifier of the humidifying unit is turned ON when the humidity inside the storage vessel becomes lower than a predetermined suitable humidity whereas the operation of the humidifier of the humidifying unit is turned OFF when the humidity inside the storage vessel exceeds the predetermined suitable humidity.

3 Claims, 3 Drawing Sheets

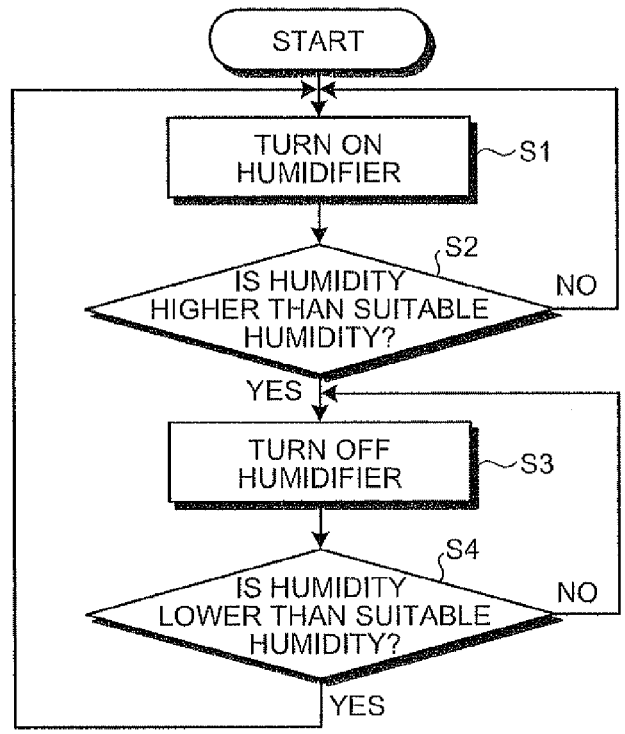
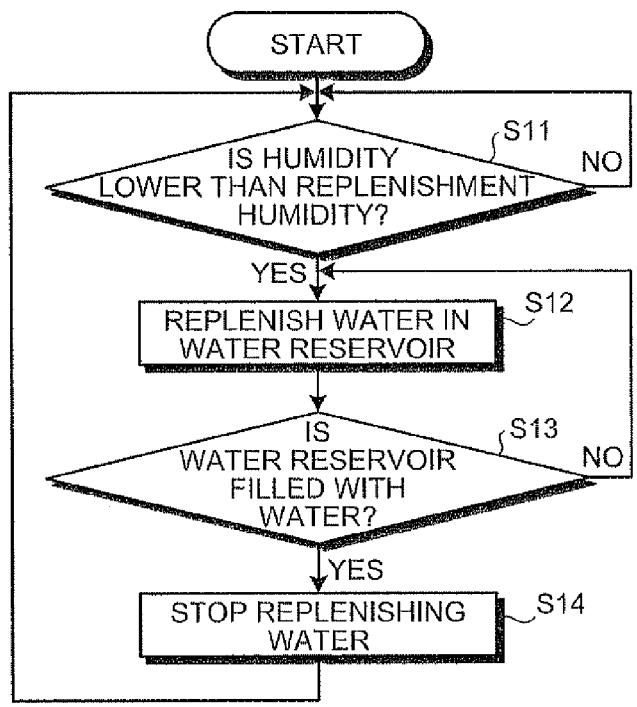

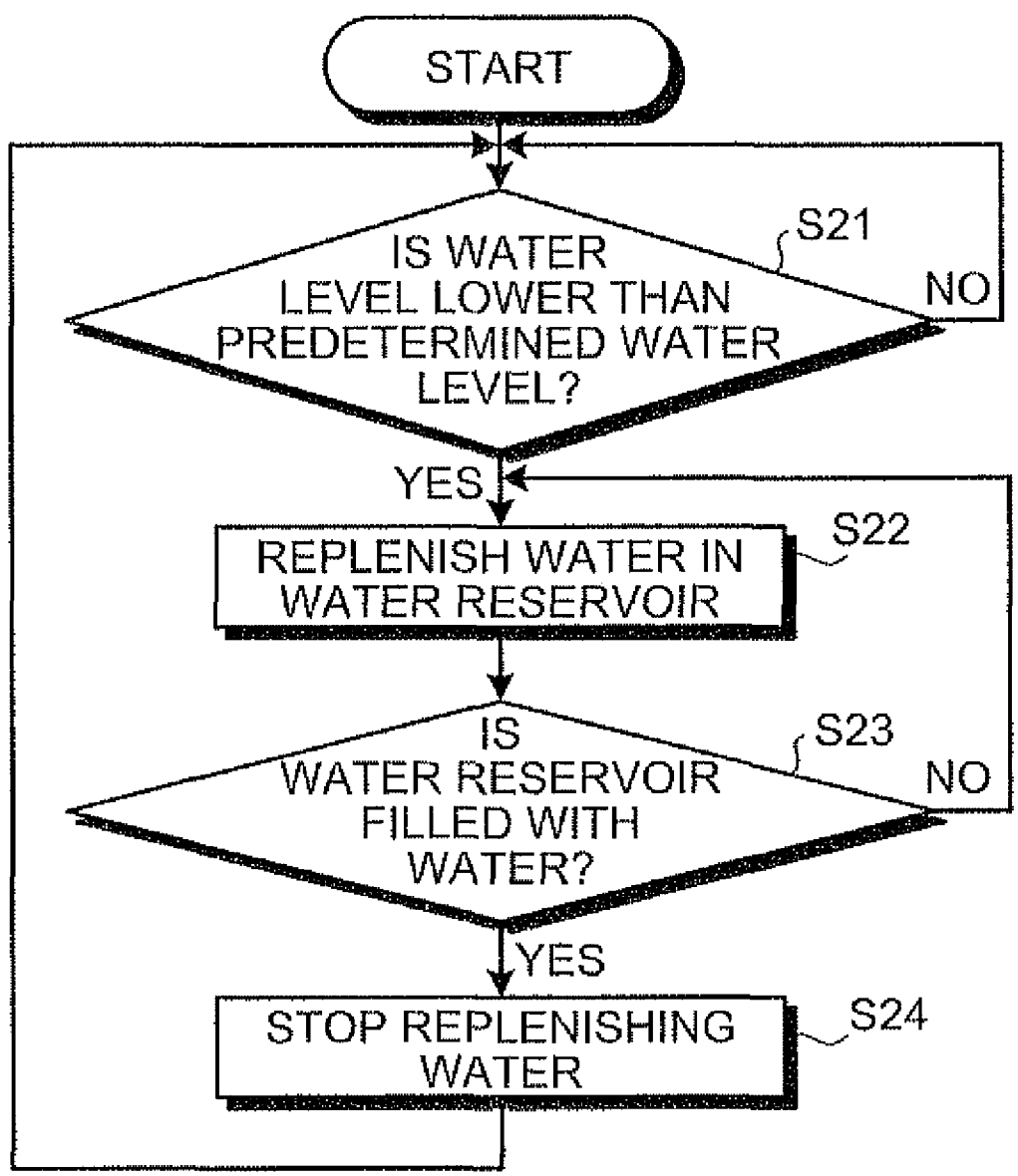

REACTION TANK

CROSS-REFERENCE TO RELATED APPLICATIONS

This application is a continuation of PCT international application Ser. No. PCT/JP2007/058068 filed Apr. 12, 2007 which designates the United States, incorporated herein by reference, and which claims the benefit of priority from Japanese Patent Application No. 2006-118095, filed Apr. 21, 2006, all incorporated herein by reference.

BACKGROUND OF THE INVENTION

1. Field of the Invention

The present invention relates to a reaction tank for causing agglutination reaction, for example, in immunological agglutination reaction.

2. Description of the Related Art

A reaction vessel (microplate) conventionally used in analysis and examination of a substance present in a specimen such as blood is formed as a plate-like vessel having plural reaction recesses called well formed and arranged in a matrix on one surface thereof. In each well of the microplate, a minute amount of specimen and reagent is dispensed to cause reaction in a reaction tank. An agglutinated substance produced by the reaction is subjected to measurement for the analysis of a substance present in the specimen.

Automatic analyzers have conventionally been proposed to automate the above-mentioned analysis. In the automatic analyzer, plural microplates are stored in a reaction line (reaction tank) until reaction time required for various types of analysis items elapses. Then, the microplate where the reaction finishes is sequentially taken out. Photometry is performed with a detector such as a CCD camera on each well, and an agglutination pattern is detected. Analysis of a substance present in the specimen is performed in such a manner (see Japanese Patent Application Laid-Open No. H5-273216, for example).

Generally, the reaction tank used in the conventional automatic analyzer as described above is configured with an evaporating dish arranged in a vessel storing the microplate. Water poured in the evaporating dish undergoes natural evaporation in the vessel to humidify an inside space of the vessel, and thereby causing agglutination reaction of the specimen in the well.

However, the humidity inside the vessel of the conventional reaction tank is difficult to control because the water in the evaporating dish is set to undergo natural evaporation. For example, if the water in the evaporating dish has not evaporated before the automatic analyzer starts analysis, humidity does not rise immediately and the start of the analysis can be delayed. In addition, when high-speed automatic analysis requires frequent transfer of the microplate in and out of the reaction tank, the humidity in the vessel of the reaction tank is difficult to maintain at a suitable level for the reaction.

SUMMARY OF THE INVENTION

It is an object of the present invention to at least partially solve the problems in the conventional technology.

A reaction tank according to one aspect of the present invention is a reaction tank for causing a reaction for analyzing a specimen in a humidity-applied atmosphere in a storage vessel, and includes a humidifying unit that includes a water reservoir reserving water and a humidifier releasing moisture of the water reservoir to an inside of the storage vessel, the humidifying unit humidifying the inside of the storage vessel, and a humidity detector that detects humidity inside the storage vessel. An operation of the humidifier of the humidifying unit is turned ON when the humidity inside the storage vessel becomes lower than a predetermined suitable humidity whereas the operation of the humidifier of the humidifying unit is turned OFF when the humidity inside the storage vessel exceeds the predetermined suitable humidity.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIGS. 3, 4, and 5 are flowcharts of an operation of the reaction tank according to the present invention.

DETAILED DESCRIPTION OF THE PREFERRED EMBODIMENTS

Exemplary embodiments of a reaction tank according to the present invention are described in detail below with reference to the accompanying drawings. The present invention is not limited by the embodiments.

Figure 1:
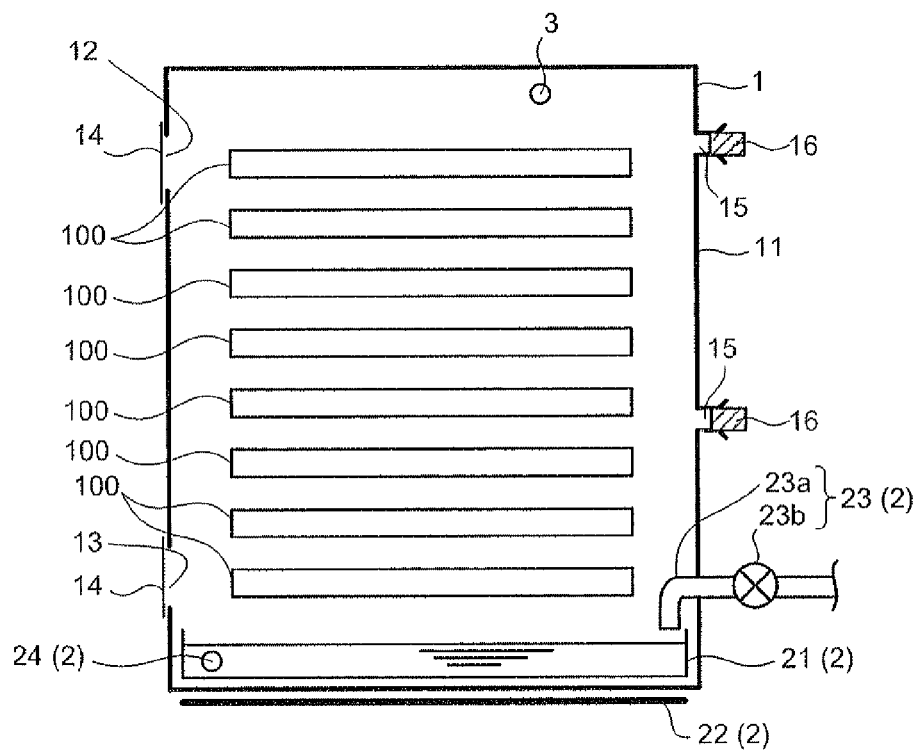
FIG. 1 is a schematic diagram of one embodiment of a reaction tank according to the present invention.

FIG. 1 is a schematic diagram of an embodiment of the reaction tank according to the present invention. The reaction tank shown in FIG. 1 is applied to an automatic analyzer (not shown) performing analysis and examination of a substance present in a specimen such as blood. In the automatic analyzer, a reaction vessel 100 (hereinafter, microplate) is employed. On one surface of the plate-like reaction vessel 100, plural reaction recesses called well (not shown) are arranged in a matrix. In the automatic analyzer, a minute amount of each of specimen and reagent is dispensed into each well of the microplate 100 to cause reaction in the reaction tank of the present invention, and photometry is performed by a detector such as a CCD camera to detect agglutination pattern in each well. Thus, the substance present in the specimen is analyzed. The reaction tank of the present invention stores the microplate 100 after a minute amount of specimen and reagent is dispensed into each well, and causes reaction of the specimen and the reagent in a desired atmosphere.

As shown in FIG. 1, the reaction tank has a storage vessel 1 which serves to store the microplate 100 in a desired atmosphere. The storage vessel 1 is configured in a box-like shape having a partition wall 11 defining an inside space of the box. The storage vessel 1 has a carry-in opening 12 for carrying in the microplate 100, and a carry-out opening 13 for carrying out the microplate 100. Each of the carry-in opening 12 and the carry-out opening 13 can be opened and closed by a door 14. Though not clearly shown, a transport mechanism is arranged in the storage vessel 1. The transport mechanism holds the microplate 100 carried in from the carry-in opening 12 and transports the microplate 100 to a position of the carry-out opening 13. In addition, though not clearly shown, a carry-in/carry-out mechanism is provided in the automatic analyzer for the storage vessel 1. The carry-in/carry-out mechanism carries in the microplate 100 from the carry-in opening 12 and carries out the microplate 100 from the carry-out opening 13.

The storage vessel 1 has a humidifying unit 2 and a humidity detector 3. The humidifying unit 2 serves to humidify the inside space of the storage vessel 1. The humidifying unit 2 has a water reservoir 21, a humidifier 22, a water replenisher 23, and a water-level detector 24.

The water reservoir 21 serves to reserve the water. In the embodiment, the water reservoir 21 is a dish-like plate whose top is open and is arranged inside the storage vessel 1 at the bottom.

The humidifier 22 serves to release moisture of the water reserved in the water reservoir 21 inside the storage vessel 1. In the embodiment, the humidifier 22 is a heater which heats and evaporates the water reserved in the water reservoir 21, and is arranged outside the storage vessel 1 at the bottom.

The water replenisher 23 serves to replenish water in the water reservoir 21. The water replenisher 23 includes a water conduit 23a which extends from the outside of the storage vessel 1 to the water reservoir 21 inside the storage vessel 1, and an on/off valve 23b which is arranged in the middle of the water conduit 23a. In the water replenisher 23, water such as tap water is supplied to the water conduit 23a. When the on/off valve 23b is opened, the water is supplied to the water reservoir 21. When the on/off valve 23b is closed, water supply to the water reservoir 21 stops.

The water-level detector 24 serves to detect the level of the water reserved in the water reservoir 21. Though not clearly shown, the water-level detector 24 may be configured with a float floating on the water reserved in the water reservoir 21 and a switch detecting a vertical position of the float, for example. Alternatively, the water-level detector 24 may be configured with a conductive switch which contacts the water reserved in the water reservoir 21. For example, the water-level detector 24 is turned into an OFF state when a sufficient amount of water is reserved in the water reservoir 21, and turned into an ON state when the amount of water reserved in the water reservoir 21 decreases. The water-level detector 21 outputs detection signals in the ON state. In the above, "when a sufficient amount of water is reserved in the water reservoir 21" means, for example, when an amount of water reserved in the water reservoir 21 is sufficient for releasing moisture in the storage vessel 1 by the humidifier 22. On the other hand, "when the amount of water reserved in the water reservoir 21 decreases" means, for example, when the amount of water reserved in the water reservoir 21 decreases to such a level that the moisture cannot be released sufficiently in the storage vessel 1 by the humidifier 22.

The humidity detector 3 is a general humidity sensor and serves to detect the humidity inside the storage vessel 1. The humidity detector 3 can be a resistance-variable-type humidity sensor which detects a change in resistance, which varies according to the change in humidity, as a change in electric signals, or a capacitance-variable-type humidity sensor in which capacitance between sensor terminals varies according to the change in humidity.

Figure 2:
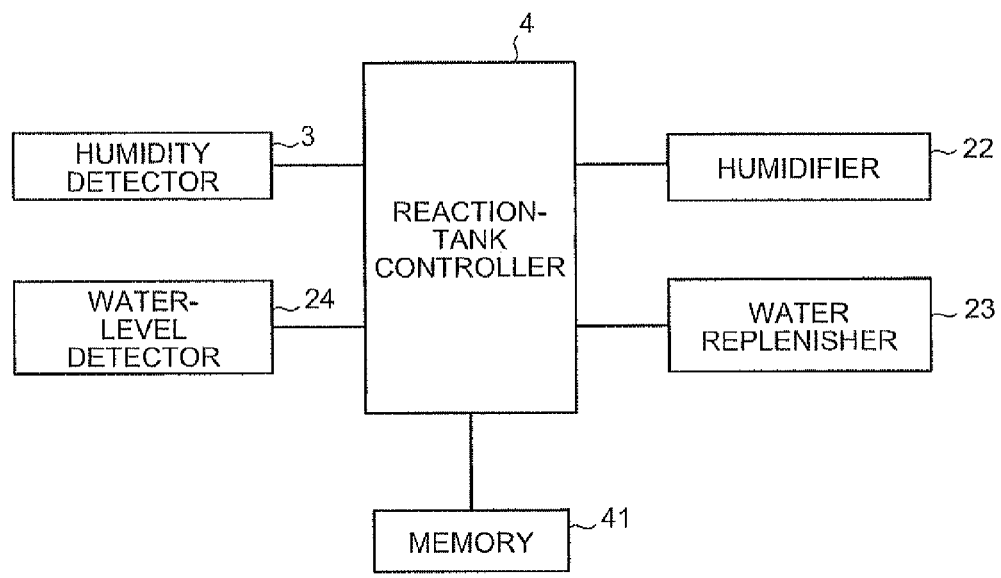
FIG. 2 is a functional block diagram of the reaction tank according to the present invention.

Operation control of the reaction tank described above is described below. FIG. 2 is a functional block diagram of the reaction tank according to the present invention, and FIGS. 3 to 5 are flowcharts of the operations of the reaction tank according to the present invention.

As shown in FIG. 2, the reaction tank has a reaction-tank controller 4. The reaction-tank controller 4 is connected to each of the humidity detector 3, the water-level detector 24, the humidifier 22, the water replenisher 23, and a memory 41.

The memory 41 stores therein in advance data and program for the reaction-tank controller 4 to control the humidifier 22 and the water replenisher 23 to keep the atmosphere inside the storage vessel 1 at a desired humidity. For example, the memory 41 stores a suitable humidity previously determined (for example, relative humidity of 80% or 80±1% to 80±5%) as a threshold, for keeping the inside of the storage vessel 1 at a predetermined level of humidity. Further, the memory 41 stores a replenishment humidity (for example, relative humidity of 60% or 60±1% to 60±5%) which is lower than the suitable humidity (relative humidity of 80% or 80±1% to 80±5%) as a threshold for causing the water replenisher 23 replenish the water in the water reservoir 21. Still further, the memory 41 stores a predetermined water level of the water level as a threshold for causing the water replenisher 23 to replenish the water in the water reservoir 21 when the water reserved in the water reservoir 21 decreases.

As shown in FIG. 3, the reaction-tank controller 4 turns ON the operation of the humidifier 22 when the analysis starts (step S1). Specifically, the reaction-tank controller 4 turns ON the power of the heater. When the humidity inside the storage vessel 1 detected by the humidity detector 3 exceeds the suitable humidity (Yes in step S2), the reaction-tank controller 4 turns OFF the operation of the humidifier 22 (step S3). Specifically, the reaction-tank controller 4 turns OFF the power of the heater. When the humidity inside the storage vessel 1 detected by the humidity detector 3 becomes lower than the suitable humidity (Yes in step S4), the reaction-tank controller 4 returns to step S1 and turns ON the operation of the humidifier 22. In brief, the reaction-tank controller 4 turns ON the operation of the humidifier 22 when the humidity inside the storage vessel 1 becomes lower than the predetermined suitable humidity, whereas turns OFF the operation of the humidifier 22 when the humidity inside the storage vessel 1 exceeds the predetermined suitable humidity. If the ON/OFF control of the humidifier 22 is a simple ON/OFF control, the humidity inside the storage vessel 1 repeatedly becomes higher and lower than the suitable humidity, and, the range of humidity variation becomes wide. Then the humidity repeatedly becomes excessive relative to the suitable humidity. Preferably, the inside of the storage vessel 1 is maintained at the suitable humidity through proportional control and PID control.

When the humidity inside the storage vessel 1 is maintained at a predetermined level as described above (in other words, when the humidifier 22 is ON), the water reserved in the water reservoir 21 gradually decreases. When the humidity inside the storage vessel 1 detected by the humidity detector 3 becomes lower than the replenishment humidity (Yes in step S11), the reaction-tank controller 4 replenishes the water in the water reservoir 21 as shown in FIG. 4 (step 12). Specifically, the water replenisher 23 opens the on/off valve 23b. In the above, "when the humidity inside the storage vessel 1 becomes lower than the replenishment humidity" means when the water in the water reservoir 21 is run out. After opening the on/off valve 23b in step S12, when the water reservoir 21 is filled with water after a predetermined time required for filling up the water reservoir 21 with water elapses (Yes in step S13), for example, the reaction-tank controller 4 stops the water replenishment by closing the on/off valve 23b (step S14). The reaction-tank controller 4 replenishes the water in the water reservoir 21 when the humidity inside the storage vessel 1 becomes lower than the predetermined replenishment humidity.

Further with regard to the water replenishment in the water reservoir 21, when the water level of the water in the water reservoir 21 detected by the water-level detector 24 becomes lower than a predetermined water level (Yes in step S21), the reaction-tank controller 4 replenishes the water in the water reservoir 21 (step S22) as shown in FIG. 5. Specifically, the water replenisher 23 opens the on/off valve 23b. Then, after opening the on/off valve 23b in step S22, when the water reservoir 21 is filled with water after a predetermined time required for filling up the water reservoir 21 with water elapses (Yes in step S23), for example, the reaction-tank controller 4 stops water replenishment by closing the on/off valve 23b (step S24). Thus, the reaction-tank controller 4 replenishes the water in the water reservoir 21 when the water level of the water reserved in the water reservoir 21 becomes lower than the predetermined water level. When the water replenishment is performed because the humidity is lower than the replenishment humidity, there is no water in the water reservoir 21. Therefore, the temperature inside the storage vessel 1 can rise because of the heater of the humidifier 22. When the water replenishment is performed because the water level is lower than the predetermined water level, the water in the water reservoir 21 has not been run out. Therefore, the temperature rise inside the storage vessel 1 can be suppressed.

Thus, the reaction tank described above can suitably control the humidity inside the storage vessel 1 so as to maintain the humidity of the storage vessel 1 at a predetermined level by turning ON the operation of the humidifier 22 when the humidity inside the storage vessel 1 becomes lower than the predetermined suitable humidity and turning OFF the operation of the humidifier 22 when the humidity inside the storage vessel 1 exceeds the predetermined suitable humidity. As a result, when the automatic analyzer starts analysis, the time until the humidity rises can be shortened. Further, even when the microplate is frequently carried in and out of the storage vessel 1, the humidity inside the storage vessel 1 can be maintained at a suitable level for the reaction.

Further, because the water is replenished in the water reservoir 21 when the humidity inside the storage vessel 1 becomes lower than the predetermined replenishment humidity, the reserve of the water in the water reservoir 21 can always be maintained and the above-described humidity control can be constantly performed. Further, since the water is replenished in the water reservoir 21 when the level of the water reserved in the water reservoir 21 becomes lower than the predetermined water level, the reserve of the water in the water reservoir 21 can always be maintained and the above-described humidity control can be constantly performed.

In the embodiment, because the humidifier 22 provided as the heater is arranged at the bottom of the storage vessel 1, temperature variation may be caused inside the storage vessel 1. Therefore, a rubber heater may be arranged over the entire partition wall 11 of the storage vessel 1, so that the rubber heater uniformly heats the storage vessel 1 and evaporates the water reserved in the water reservoir 21. Further, the external surface of the storage vessel 1 is preferably covered with a heat insulating material to eliminate the temperature variation.

In the embodiment, the humidifier 22 provided as the heater heats and evaporates the water reserved in the water reservoir 21. The present invention, however, is not limited by the above-described configuration. For example, the humidifier 22 may be configured to atomize the water reserved in the water reservoir 21 by ultrasonic vibrations and release the atomized water inside the storage vessel 1. When the water reserve in the water reservoir 21 is atomized by the ultrasonic vibrations and released inside the storage vessel 1, the temperature variation mentioned above can be prevented. In the embodiment, the water reservoir 21 is arranged inside the storage vessel 1. Alternatively, the water reservoir 21 and the humidifier 22 may be arranged outside the storage vessel 1 and only the moisture may be supplied inside the storage vessel 1. When the water reservoir 21 and the humidifier 22 are arranged outside the storage vessel 1, the internal configuration of the storage vessel 1 can be simplified, and the temperature variation which can be caused by the humidifier 22 provided as the heater can be prevented.

The reaction tank as described above may be configured to allow temperature/humidity validation. For example, a hole 15 may be formed in the partition wall 11 of the storage vessel 1 as shown in FIG. 1, so that the inside space and the outside space of the storage vessel 1 are communicated with each other. In a normal condition where the storage vessel 1 is used as a reaction tank, the hole 15 is blocked by a plug 16. At the time of validation, an operator pulls off the plug 16 and inserts an external thermohygrometer (not shown) through the hole 15 to the inside of the storage vessel 1 so as to acquire validation data. As a result, the temperature/humidity validation can be performed, and the humidity detector 3 can be corrected. The hole 15 blocked by the plug 16 is preferably arranged at such a position that the external thermohygrometer (not shown) can be brought close to the humidity detector 3. Further, preferably the hole 15 blocked by the plug 16 is formed at plural positions so that the validation can be performed at plural positions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A reaction tank for causing a reaction for analyzing a specimen in a humidity-applied atmosphere, comprising:
    a storage vessel containing the humidity-applied atmosphere, the storage vessel having a carry-in opening and a carry-out opening, each opening having a respective door operable to be opened and closed;
    a humidifying unit that includes a water reservoir reserving water and a humidifier releasing moisture of the water reservoir to an inside of the storage vessel, the humidifying unit humidifying the inside of the storage vessel;
    a transport mechanism configured for carrying a microplate holding the specimen into the storage vessel through the carry-in opening and for carrying the microplate out of the storage vessel through the carry-out opening; and
    a humidity detector that detects humidity inside the storage vessel,
    an operation of the humidifier of the humidifying unit being turned ON when the humidity inside the storage vessel becomes lower than the predetermined suitable humidity whereas the operation of the humidifier of the humidifying unit being turned OFF when the humidity inside the storage vessel exceeds the predetermined suitable humidity,
    wherein the reaction tank maintains a predetermined suitable humidity within the storage vessel even when the microplate is frequently carried in and out of the storage vessel.

2. The reaction tank according to claim 1, wherein
    the humidifying unit includes a water replenisher that replenishes water in the water reservoir, and the water replenisher replenishes the water in the water reservoir when the humidity inside the storage vessel becomes lower than a predetermined replenishment humidity.

3. The reaction tank according to claim 1, wherein the humidifying unit includes a water replenisher that replenishes water in the water reservoir and a water level detector that detects a water level of water reserved in the water reservoir, and the water replenisher replenishes water in the water reservoir when the water level of the water reserved in the water reservoir becomes lower than a predetermined water level.

* * * * *